US011752156B2

(12) United States Patent
Lau et al.

(10) Patent No.: US 11,752,156 B2
(45) Date of Patent: Sep. 12, 2023

(54) COMPOSITIONS AND METHODS FOR TREATING HYPERPROLIFERATIVE SKIN DISORDERS

(71) Applicant: Athenex HK Innovative Limited, Hong Kong (HK)

(72) Inventors: Johnson Yiu-Nam Lau, Houston, TX (US); Alissa Rae Verone-Boyle, Kenmore, NY (US); Chun-Ho Wong, Shatin (HK); Yahao Bu, Williamsville, NY (US); Murray John Cutler, Fort Erie (CA); Krista Elizabeth Belko, Clarence Center, NY (US); Min-Fun Rudolf Kwan, Summit, NJ (US)

(73) Assignee: Athenex HK Innovative Limited, Sha Tin (HK)

( * ) Notice: Subject to any disclaimer, the term of this patent is extended or adjusted under 35 U.S.C. 154(b) by 11 days.

(21) Appl. No.: 16/978,037

(22) PCT Filed: Mar. 6, 2019

(86) PCT No.: PCT/US2019/021037
§ 371 (c)(1),
(2) Date: Sep. 3, 2020

(87) PCT Pub. No.: WO2019/173533
PCT Pub. Date: Sep. 12, 2019

(65) Prior Publication Data
US 2021/0038608 A1 Feb. 11, 2021

Related U.S. Application Data

(60) Provisional application No. 62/639,742, filed on Mar. 7, 2018.

(51) Int. Cl.
*A61K 31/5377* (2006.01)
*A61K 31/593* (2006.01)
*A61P 17/06* (2006.01)
*A61P 17/00* (2006.01)
*A61N 5/06* (2006.01)
*A61K 9/00* (2006.01)
*A61K 45/06* (2006.01)

(52) U.S. Cl.
CPC ........ *A61K 31/5377* (2013.01); *A61K 31/593* (2013.01); *A61N 5/062* (2013.01); *A61N 5/0616* (2013.01); *A61K 9/0014* (2013.01); *A61K 45/06* (2013.01); *A61N 2005/0661* (2013.01)

(58) Field of Classification Search
CPC ..... C07D 401/12; C07D 401/14; A61P 31/18; A61P 31/007; C07K 45/06
USPC ............................ 514/266.21, 300, 333, 338
See application file for complete search history.

(56) References Cited

U.S. PATENT DOCUMENTS

| | | | |
|---|---|---|---|
| 7,939,529 B2 | 5/2011 | Hangauer | |
| 10,617,693 B2* | 4/2020 | Kwan | ..................... A61P 17/00 |
| 2001/0002396 A1 | 5/2001 | Achkar | |
| 2012/0270874 A1 | 10/2012 | Hangauer | |
| 2017/0196949 A1 | 7/2017 | Essen-Moller | |
| 2018/0256589 A1* | 9/2018 | Kwan | ................ A61K 31/5377 |

FOREIGN PATENT DOCUMENTS

| WO | 2014194133 | 12/2014 |
|---|---|---|
| WO | 2016193441 | 12/2016 |

OTHER PUBLICATIONS

Seckin D,.et al .(J Drugs Dermatol. May 2009;8(5):451-4. PMID: 19537367; .Can topical calcipotriol be a treatment alternative in actinic keratoses?A preliminary report).*
Scott, Lesley J., Christopher J. Dunn, and Karen L. Goa. "Calcipotriol ointment: a review of its use in the management of psoriasis." American journal of clinical dermatology 2.2 (2001): 95-120. (Year: 2001).*
Dubertret L, Wallach D, Souteyrand P, et al. Efficacy and safety of calcipotriol (MC 903) ointment in psoriasis vulgaris. A randomized, double-blind, right/left comparative, vehicle-controlled study. J Am Acad Dermatol. 1992;27(6 Pt 1):983-988. doi:10.1016/0190-9622(92)70299-u.
Segaert S, Duvold LB. Calcipotriol cream: a review of its use in the management of psoriasis. J Dermatolog Treat. 2006;17(6):327-337. doi:10.1080/09546630600999219.
Kinex Pharmaceuticals, "Kinex Pharmaceuticals Announces Allowance of the Investigational New Drug (IND) application for KX2-391 Ointment by the United States Food and Drug Administration (FDA)," https://www.prnewswire.com/news-releases/kinex-pharmaceuticals-announces-allowance-of-the-investigational-new-drug-ind-application-for-kx2-391-ointment-by-the-united-states-food-and-drug-administration-fda-268466522.html.

(Continued)

*Primary Examiner* — Bethany P Barham
*Assistant Examiner* — Peter Anthopolos
(74) *Attorney, Agent, or Firm* — Fish IP Law, LLP

(57) ABSTRACT

Compositions and methods are provided that are effective in treating skin hyperproliferative disorders. These include a topical pharmaceutical preparation that includes a compound that has two or more of a SRC-kinase inhibiting activity, a tubulin polymerization inhibiting activity, an activity that arrests the cell cycle at G2/M, and an activity that induces apoptosis. The compound KX01 is provided as an example of such a compound. The topical pharmaceutical preparation further includes a vitamin D derivative or a retinoid, where the combination provides a synergistic effect. Use of the topical pharmaceutical preparation can be combined with exposure to blue, UVA, or UVB light, which provides a synergistic effect.

8 Claims, 8 Drawing Sheets

(56) References Cited

OTHER PUBLICATIONS

Kragballe K. Treatment of Psoriasis by the Topical Application of the Novel Cholecalciferol Analogue Calcipotriol (MC 903). Arch Dermatol. 1989;125(12):1647-1652. doi:10.1001/archderm.1989.01670240047011.
Kinex Pharmaceuticals, Kinex Pharmaceuticals Announces Allowance of the Investigational New Drug(IND) application for KX2-391 Ointment bythe United States Food and Drug Administration (FDA). Jul. 2014. 3 pages.
Cunningham, et al. "Randomized trial of calcipotriol combined with 5-fluorouracil for skin cancer precursor immunotherapy," J Clin Invest. 2017;127(1):106-116. https://doi.org/10.1172/JCI89820. 12 pages.
Gaukroger, et al. "Cytotoxicity of etretinate and vindesine," Br. Cancer (1985), 52, 369-375. 7 pages.
Halverstam, et al. "Nonstandard and off-label therapies for psoriasis," Clinics in Dermatology (2008) 26, 546-553. 8 pages.
Hermann, et al. "The retinoid X receptor agonist bexarotene (Targretin) synergistically enhances the growth inhibitory activity of cytotoxic drugs in non-small cell lung cancer cells," Lung Cancer (2005) 50, 9-18. 10 pages.
Torsekar, et al. "Topical Therapies in Psoriasis," Indian Dermatol Online J 2017;8:235-45. 11 pages.
Van de Kerkhof, Peter C. M. "An Update on Topical Therapies for Mild-Moderate Psoriasis," Dermatol Clin 33 (2015) 73-77. 5 pages.

* cited by examiner

COMPOSITIONS AND METHODS FOR TREATING HYPERPROLIFERATIVE SKIN DISORDERS

This application claims the benefit of U.S. Provisional Application No. 62/639,742 filed on Mar. 7, 2018. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is combination therapies for treating hyperproliferative skin disorders.

BACKGROUND

The following description includes information that may be useful in understanding the present invention. It is not an admission that any of the information provided herein is prior art or relevant to the presently claimed invention, or that any publication specifically or implicitly referenced is prior art.

The background description includes information that may be useful in understanding the present invention. It is not an admission that any of the information provided herein is prior art or relevant to the presently claimed invention, or that any publication specifically or implicitly referenced is prior art.

Cell proliferation disorders of the skin such as psoriasis, actinic keratosis, and non-melanoma skin cancers (e.g., basal cell carcinoma and squamous cell carcinoma) are common, but treatments often lack the desired effectiveness, have inconvenient dosing regimens, and/or have severe side effects.

Current pharmaceutical approaches to treating skin proliferation disorders (such as psoriasis) include the use of corticosteroids, vitamin D analogs, and retinoids. In some instances phototherapy is used to treat skin proliferation disorders, and can be used in combination with pharmaceutical interventions. Phototherapy typically involves exposure to UVB and/or UVA light, and can include treatment with photosensitizers (e.g. using psoralen in combination with exposure to UVA light).

More recently, biologics have been used to treat skin proliferative disorders. These are typically monoclonal antibodies or antibody fragments that target specific components of the immune system or cytokines involved in inflammation. Examples of such biologics include Humira™, Amevive™, ABT-874, Enbrel™, Remicade™, and Stelara™. Unfortunately such biologics are and expensive, and the use of such biologics is associated with increased incidence of cancer and certain types of infection.

Actinic keratoses are common pre-cancerous skin lesions that show excessive proliferation of skin cells, and are the third most common reason for consulting a dermatologist. These can be treated by excision, freezing, and/or the application of pharmaceutical agents to the lesion. Drugs used to treat these lesions include 5-fluorouracil (5-FU), diclofenac, ingenol, and imiquimod, Unfortunately, side effects (which include discomfort, redness, and blistering) and/or inconvenient dosing regimens limit patient compliance, and therefore, the efficacy of these approaches.

Calcipotriol is an FDA-approved topical medication for treatment of skin hyperproliferative disorders, and is hypothesized to act via induction of thymic stromal lymphopoietin ("TSLP") expression. The immune effects of TSLP expression have been shown to include antitumor immunity in barrier-defective skin (see Trevor J. Cunningham et al., Randomized trial of calcipotriol combined with 5-fluorouracil for skin cancer precursor immunotherapy, 127(1) J. Clinical Investigation 106-16 (2017)). All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Calcipotriol has been used in combination with other drugs. For example, treatment with calcipotriol ointment combined with 5-fluorouracil cream can decrease the number of actinic keratoses compared to treatment with 5-fluorouracil alone. The combined use of calcipotriol ointment and 5-fluorouracil cream on face, scalp, or upper extremities has been found to induce TSLP, HLA class II, and natural killer cell group 2D ligand expression in keratinocytes of these lesions. Calcipotriol and 5-fluorouracil are thought to activate a CD4+ T cell-mediated immunity against actinic keratosis. However, this treatment regiment maintains the limitations of 5-fluorouracil, including side effects that limit patient compliance.

Thus, there is still a need for treatments for cell hyperproliferation disorders that are both effective and well tolerated.

SUMMARY OF THE INVENTION

The inventive subject matter provides apparatus, systems and methods in which a—

One embodiment of the inventive concept is a pharmaceutical composition that includes a first compound having an SRC-kinase inhibition activity, an inhibition of tubulin polymerization activity, a cell cycle arrest at G2/M activity, and/or a induction of apoptosis activity, and a second compound this is a vitamin D analog or a retinoid, where the first compound and the second compound are present in amounts sufficient to treat a hyperproliferative disorder in an affected area. Such composition can be formulated for topical application, for example as a foam, a cream, a paste, an ointment, a gel, a solution, a liquid suspension, a droplet suspension, an aerosol, and/or a powder. The vitamin D analog can also have a G0/G1 arrest activity, an anti-proliferation activity, an anti-inflammation activity, an induction of keratinocyte differentiation activity, an activity that decreases the number of pro-inflammatory T-cells, an apoptosis inducing activity.

In such a compositions the first compound can have a structure according to Formula I.

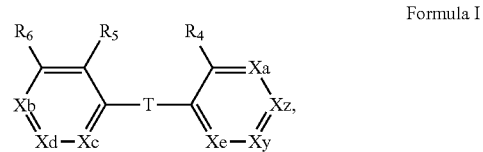

Formula I or a salt, solvate, hydrate, or prodrug thereof, wherein: T is a bond;
Xy is CZ, CY, N, or N—O;
Xz is CZ, CY, N, or N—O;
at least one of Xy and Xz is CZ;
Y is selected from hydrogen, hydroxyl, halogen, ($C_1$, $C_2$, $C_3$, $C_4$, $C_5$, or $C_6$) alkyl, $C_1$, $C_2$, $C_3$, $C_4$, $C_5$, or $C_6$ alkoxy, O—($C_1$, $C_2$, $C_3$, $C_4$, $C_5$, or $C_6$) alkylaryl, and O-benzyl;
Xa is CRa or N, or N—O;
Xb is CRb, N, or N—O;
Xc is CRc or N, or N—O;
Xd is CRd or N, or N—O;
Xe is CRe, N, or N—O
Ra, Rb, Rc, Rd, Re, $R_4$, $R_5$, and $R_6$ are, independently, hydrogen, hydroxyl, halogen, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$alkyl-O—($C_1$, $C_2$, $C_3$, $C_4$, $C_5$, or $C_6$) alkyl, COOH, COO—($C_1$, $C_2$, $C_3$, $C_4$, $C_5$, or $C_6$) alkyl, $SO_2H$, $SO_2$ ($C_1$, $C_2$, $C_3$, $C_4$, $C_5$, or $C_6$) alkyl,

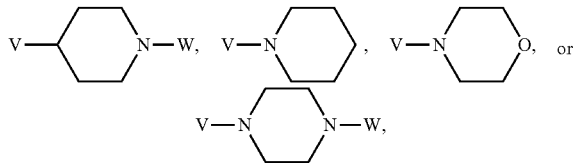

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;
V is a bond, —$CH_2$—, —$CH_2CH_2$—, —$CH_2CH_2CH_2$—, —O—$CH_2$—, —$OCH_2CH_2$— or —$OCH_2CH_2CH_2$—;
$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl;
Z is: $(CHR_1)_n$—C(O)—$NR_2(CHR_3)_m$—Ar, where Ar is a substituted or unsubstituted aryl or nitrogen-containing heteroaryl group, $R_1$, $R_2$, and $R_3$ are independently H or $C_1$, $C_2$, $C_3$, $C_4$, $C_5$, or $C_6$ alkyl;
n is 0, 1, or 2; and
m is 1 or 2,
wherein at least one of Xa, Xb, Xc, Xd and Xe is N.

In a preferred embodiment the first compound can be KX01, which has the structure shown in Formula 2.

Formula 2

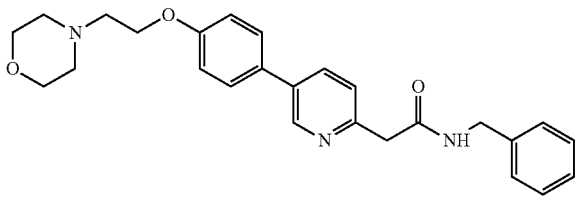

In such a composition the second compound can be a vitamin D3 analog, such as calcipotriol (calipotriene). The composition can be formulated to provide a molar ratio of the first compound to the second compound of from 160:3 to 5:243 at the affected area. In some embodiments the composition this molar ratio is selected to provide an effect at the affected area that exceeds the additive effect of the first compound and the second compound when applied individually at corresponding concentrations. In other embodiments the second compound is a retinoid, such as an acetylenic retinoid or tazarotene. In some embodiments the second compound is a vitamin D analog, and the composition also includes a retinoid.

Another embodiment of the inventive concept is a method of treating a skin condition (such as actinic keratosis or psoriasis) by providing a topical preparation (e.g. a foam, a cream, a paste, an ointment, a gel, a solution, a liquid suspension, a droplet suspension, an aerosol, and/or a powder) that includes a first compound and a second compound, where the first compound has at least two of an SRC-kinase inhibiting activity, a tubulin polymerization inhibiting activity, a cell cycle arrest at G2/M activity, and/or an activity that induces apoptosis, and where the second compound includes a vitamin D analog (such as a vitamin D3 analog or calcipotriol) or a retinoid (such as an acetylenic retinoid or tazarotene), where the first compound and the second compound are present in amounts sufficient to provide a reduction or elimination of a hyperproliferative disorder in an affected area. The molar ratio molar ratio of the first compound to the second compound can range from 160:3 to 5:243 or from 1:1 to 1:2,500 at the affected area. In some embodiments the first compound can be KX01 (as described above). In some embodiments the second compound is a vitamin D3 analog or calcipotriol (calcipotriene). In some embodiments the second compound is a vitamin D analog, and the topical composition also includes a retinoid. The method also includes a step of applying the topical preparation to an area affected by the skin condition on a schedule that is effective to treat the skin condition (e.g. from once a week to four times a day). Skin conditions that can be treated in this fashion include actinic keratosis and psoriasis. The vitamin D analog can have a G0/G1 arresting activity, an anti-proliferation activity, an anti-inflammatory activity, an activity that induces keratinocyte differentiation, an activity that decreases the number of pro-inflammatory T-cells, and/or an activity that induces apoptosis. The retinoid can have an activity that induces keratinocytes proliferation, modulates epidermal differentiation, stimulates extracellular matrix production, and/or alters sebocyte differentiation. In a preferred embodiment the first topical composition includes the first compound in a first amount and the second topical composition comprises the second compound in a second amount, where the first amount and the second amount are selected to provide a combined therapeutic effect. This combined therapeutic effect is greater than the sum of the therapeutic effects provided by application of the first compound at the first amount and by application of the second compound at the second amount.

Another embodiment of the inventive concept is a kit for treating a skin cell hyperproliferation disorder, having a first topical composition that includes a first compound (such as KX01, as shown above) with two or more of a SRC-kinase inhibiting activity, a tubulin polymerization inhibiting activity, an activity that arrests the cell cycle at G2/M, and an activity that induces apoptosis, along with a second topical composition that includes a second compound such as a vitamin D analog (such as a vitamin D3 analog and/or calcipotriol) or a retinoid (such as an acetylenic retinoid and/or tazarotene). In some embodiments the kit includes both a vitamin D analog and a retinoid. The first compound and the second compound are present in their respective topical compositions in amounts sufficient to provide a reduction or elimination of the skin cell hyperproliferation disorder when the first and second topical compositions are applied individually according to schedule. The molar ratio molar ratio of the first compound to the second compound can range from 160:3 to 5:243 or from 1:1 to 1:2,500. Such topical compositions can be provided as a foam, a cream, a paste, an ointment, a gel, a solution, a liquid suspension, a droplet suspension, an aerosol, and/or a powder. In a preferred embodiment the first topical composition includes the first compound in a first amount and the second topical composition comprises the second compound in a second amount, where the first amount and the second amount are selected to provide a combined therapeutic effect. This combined therapeutic effect is greater than the sum of the therapeutic effects provided by application of the first compound at the first amount and by application of the second compound at the second amount.

Another embodiment of the inventive concept is a method of increasing two or more of a SRC-kinase inhibiting activity, a tubulin polymerization inhibition activity, an activity that arrests the cell cycle at G2/M, and an activity that induces apoptosis produced by a first compound in a pharmaceutical composition. This is accomplished by including a second compound (such as a vitamin D analog or a retinoid) in the pharmaceutical composition, where the molar ratio of the first compound and the second compound is selected to enhance the activities in more than an additive manner. The molar ratio molar ratio of the first compound to the second compound can range from 160:3 to 5:243 or from 1:1 to 1:2,500. The first compound can be KX01 (as shown above). The vitamin D analog can be a vitamin D3 analog and/or calcipotriol. The retinoid can be an acetylenic retinoid and/or tazarotene. In embodiments where the second compound is a vitamin D analog the composition can further include a retinoid.

Another embodiment of the inventive concept is the use of a first compound (such as Kx)1, as shown above) and a second compound in preparing an medicament for treating a skin condition (such as actinic keratosis and/or psoriasis), where the first compound has two or more of a SRC-kinase inhibiting activity, a tubulin polymerization activity, an activity that arrests the cell cycle at G2/M, and an activity that induces apoptosis, and where the second compound includes a vitamin D analog (e.g. a vitamin D3 analog and/or calcipotriol) or a retinoid (e.g. an acetylenic retinoid and/or tazarotene). The first compound and the second compound are present in the medicament in amounts sufficient to provide a reduction or elimination of a hyperproliferative disorder by applying the medicament to an area affected by the skin condition on a schedule effective to treat the skin condition (e.g. at a frequency of once a week to four times a day). The molar ratio molar ratio of the first compound to the second compound can range from 160:3 to 5:243 or from 1:1 to 1:2,500. The vitamin D analog can be selected to have a G0/G1 arresting activity, an anti-proliferation activity, an anti-inflammation activity, an activity that induces keratinocyte differentiation, an activity that decreases the number of pro-inflammatory T-cells, and/or an activity that induces of apoptosis. In embodiments where the second compound is a vitamin D analog the medicament can further include a retinoid. Such a medicament can be formulated to be used for topical application, for example as a foam, a cream, a paste, an ointment, a gel, a solution, a liquid suspension, a droplet suspension, an aerosol, and/or a powder. In a preferred embodiment the medicament includes the first compound in a first amount and the second compound in a second amount, where the first amount and the second amount are selected to provide a combined therapeutic effect. This combined therapeutic effect is greater than the sum of the therapeutic effects provided by application of the first compound at the first amount and by application of the second compound at the second amount.

Another embodiment of the inventive concept is a method of treating a proliferative condition (e.g. actinic keratosis and/or psoriasis) by providing a topical preparation that includes a first compound, where the first compound (e.g. KX01, as shown above) has two or more of a SRC-kinase inhibiting activity, a tubulin polymerization inhibiting activity, an activity that arrests the cell cycle at G2/M, and an activity that induces apoptosis and applying the topical preparation to an area affected by the skin condition on a schedule effective to treat the skin condition, in combination with directing a blue light (e.g. having a wavelength from 280 nm to 500 nm, which can be provided as either a narrow or broad band emission) onto the area affected by the skin condition at a specified light flux and for a specified exposure time. Suitable light sources include LED/LCD and fluorescent lights, and can emit visible blue light (e.g. 311 nm to 460 nm), UVA, and/or UVB). The topical preparation can be formulated as formulated as a foam, a cream, a paste, an ointment, a gel, a solution, a liquid suspension, a droplet suspension, an aerosol, and/or a powder. In some embodiments the topical preparation further includes a vitamin D analog (e.g. a vitamin D3 analog and/or calcipotriol) and/or a retinoid (e.g. an acetylenic retinoid and/or tazarotene). In such embodiments the retinoid can have an activity that induces keratinocytes to proliferate, an activity that modulates epidermal differentiation, an activity that stimulates extracellular matrix production, and/or an activity that alters of sebocyte differentiation. In some embodiments the topical preparation includes the first compound (and second compound, if present) in an amount(s) that provides a first therapeutic effect and the specified light flux and exposure time are provided that can produce a second therapeutic effect, however the method provides a third therapeutic effect that is greater than the sum of a first therapeutic effect and the second therapeutic effect.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
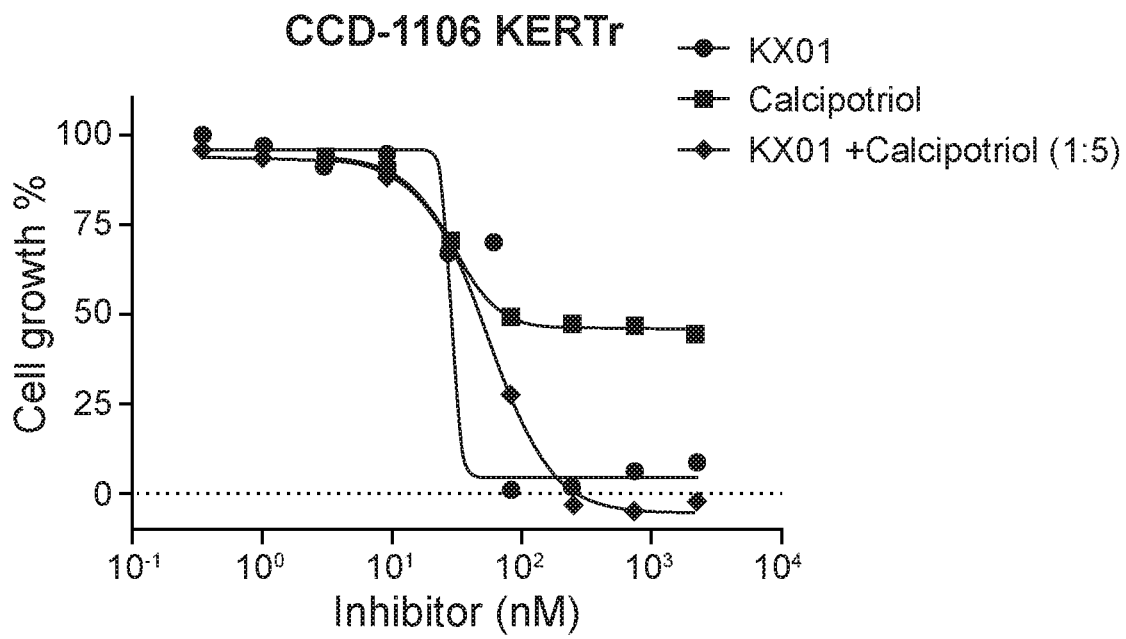
FIG. 1: Results of an experiment comparing cell growth in response to KX01, Calcipotriol, and KX01+calcipotriol at a 1:5 ratio.

The inventive subject matter provides compositions and methods in which a vitamin D analog synergistically enhances the antiproliferative effects of an antiproliferative compound for the treatment of cell hyperproliferation disorders, particularly dermatological disorders characterized by increased proliferation of skin cells (e.g. psoriasis, actinic keratosis, etc.).

Within the context of this application the term Imax refers to the maximal inhibitory concentration of a compound or therapy, the term IC50 refers to a value at which 50% of the maximum inhibitory effect realized is achieved, and the term H is related to the steepness of the slope of a calculated curve or surface derived from a mathematical model.

Various objects, features, aspects and advantages of the inventive subject matter will become more apparent from the following detailed description of preferred embodiments, along with the accompanying drawing figures.

The inventive subject matter includes pharmaceutical compositions that include a first compound that exhibits at least two of: SRC-kinase inhibition, inhibition of tubulin polymerization, cell cycle arrest at G2/M, and induction of apoptosis. The pharmaceutical composition further includes a second compound that is a vitamin D analog and/or a retinoid (i.e. a retinoid or retinoid analog). The first and second compounds are present in the pharmaceutical composition in amounts sufficient to treat a cell hyperproliferation disorder, such actinic keratosis or psoriasis. In preferred embodiments the first and second compounds are present in amounts that provide a synergistic effect on inhibition of proliferation/growth of skin cells relative to their individual contributions. In some embodiments such drug combinations can be used in combination with controlled exposure to light, for example blue light (e.g. 280 nm to 500 nm light), UV/A light, and/or UV/B light.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The first compound can be an antiproliferative compound as described in U.S. Pat. No. 8,003,641 to David G. Hangauer, Jr., filed Apr. 26, 2007, which is incorporated herein by reference. Exemplary compounds have the structure(s) shown below. Specifically, suitable compounds include those having Formula I:

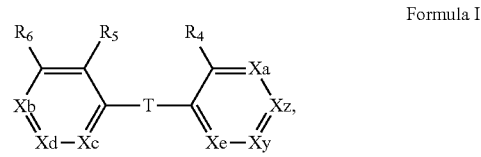

Formula I or a salt, solvate, hydrate, or prodrug thereof, wherein: T is a bond;

Xy is CZ, CY, N, or N—O;

Xz is CZ, CY, N, or N—O;

at least one of Xy and Xz is CZ;

Y is selected from hydrogen, hydroxyl, halogen, ($C_1$, $C_2$, $C_3$, $C_4$, $C_5$, or $C_6$) alkyl, $C_1$, $C_2$, $C_3$, $C_4$, $C_5$, or $C_6$ alkoxy, O—($C_1$, $C_2$, $C_3$, $C_4$, $C_5$, or $C_6$) alkylaryl, and O-benzyl;

Xa is CRa or N, or N—O;
Xb is CRb, N, or N—O;
Xc is CRc or N, or N—O;
Xd is CRd or N, or N—O;
Xe is CRe, N, or N—O
Ra, Rb, Rc, Rd, Re, $R_4$, $R_5$, and $R_6$ are, independently, hydrogen, hydroxyl, halogen, $C_1$, $C_2$, $C_3$, $C_4$, $C_5$, or $C_6$ alkoxy, O-lower ($C_1$, $C_2$, $C_3$, $C_4$, $C_5$, or $C_6$) alkyl-aryl, O-benzyl, $C_1$, $C_2$, $C_3$, $C_4$, $C_5$, or $C_6$ alkyl-OH, $C_1$, $C_2$, $C_3$, $C_4$, $C_5$, or $C_6$alkyl-O—($C_1$, $C_2$, $C_3$, $C_4$, $C_5$, or $C_6$) alkyl, COOH, COO—($C_1$, $C_2$, $C_3$, $C_4$, $C_5$, or $C_6$) alkyl, $SO_2H$, $SO_2$ ($C_1$, $C_2$, $C_3$, $C_4$, $C_5$, or $C_6$) alkyl,

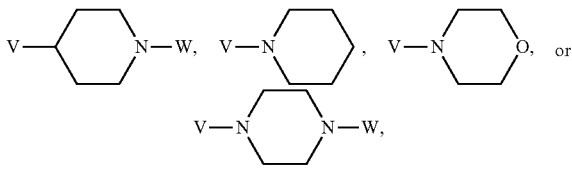

where W is H, or $C_1$, $C_2$, $C_3$, $C_4$, $C_5$, or $C_6$ alkyl, $C_1$, $C_2$, $C_3$, $C_4$, $C_5$, or $C_6$ alkyl-aryl;
V is a bond, —$CH_2$—, —$CH_2CH_2$—, —$CH_2CH_2CH_2$—, —O—$CH_2$—, —$OCH_2CH_2$— or —$OCH_2CH_2CH_2$—;
$R_{12}$, $R_{13}$, $R_{14}$, $R_{15}$, $R_{16}$, $R_{17}$, and $R_{18}$, are, independently, H or $C_1$, $C_2$, $C_3$, $C_4$, $C_5$, or $C_6$ alkyl;
Z is: $(CHR_1)_n$—C(O)—$NR_2(CHR_3)_m$—Ar, where Ar is a substituted or unsubstituted aryl or nitrogen-containing heteroaryl group, $R_1$, $R_2$, and $R_3$ are independently H or $C_1$, $C_2$, $C_3$, $C_4$, $C_5$, or $C_6$ alkyl;
n is 0, 1, or 2; and
m is 1 or 2,
wherein at least one of Xa, Xb, Xc, Xd and Xe is N.

In a preferred embodiment of the inventive subject matter, the first compound is KX01 (N-benzyl-2-(5-{4-[2-(morpholine-4-yl)ethoxy]phenyl}pyridine-2-yl)acetamide. The chemical structure of KX01 is represented by Formula 2:

Formula 2

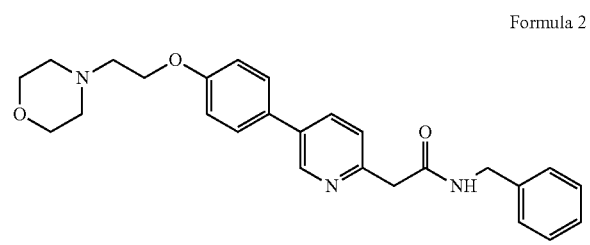 [SMILES: O=C(Cc1ccc(-c2ccc(OCCN3CCOCC3)cc2)cn1)NCc1ccccc1]

KX01 has been shown to inhibit SRC-kinase, inhibits tubulin polymerization, and induces apoptosis by G2/M arrest.

Suitable vitamin D analogs include calcipotriol in preferred embodiments of the inventive subject matter. Calcipotriol is a vitamin D3 analog that has been observed to induce apoptosis in a variety of cell types. Without wishing to be bound by a particular theory, the inventors hypothesize that the combination of an antiproliferative compound with a vitamin D analog is beneficial, because they have different mechanisms of action that target two different phases of the cell cycle.

Surprisingly, the inventors identified synergistic (e.g., more than additive) effects in regards to inhibition of skin cell proliferation/growth when such compounds are used together. Advantageously, combining KX01 and calcipotriol expands the clinical utility of KX01 ointment to the treatment of hyperproliferative skin disorders, while synergistic effects can provide for increased effectiveness and/or reduced dosages.

Figure 2:
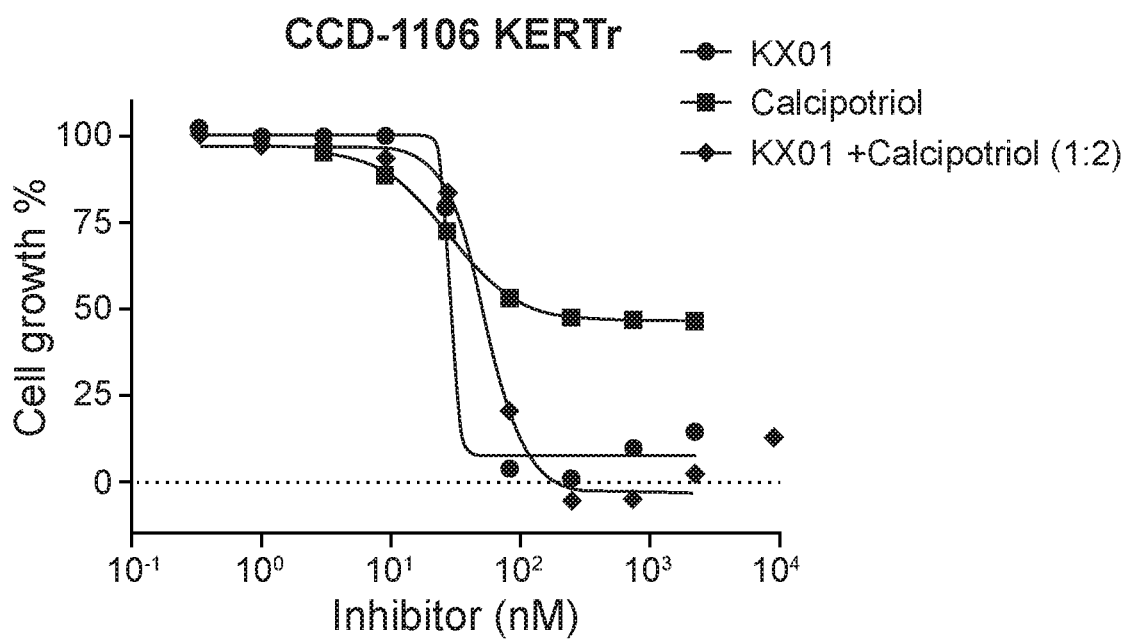
FIG. 2: Results of an experiment comparing cell growth in response to KX01, Calcipotriol, and KX01+calcipotriol at a 1:2 ratio.
Figure 3:
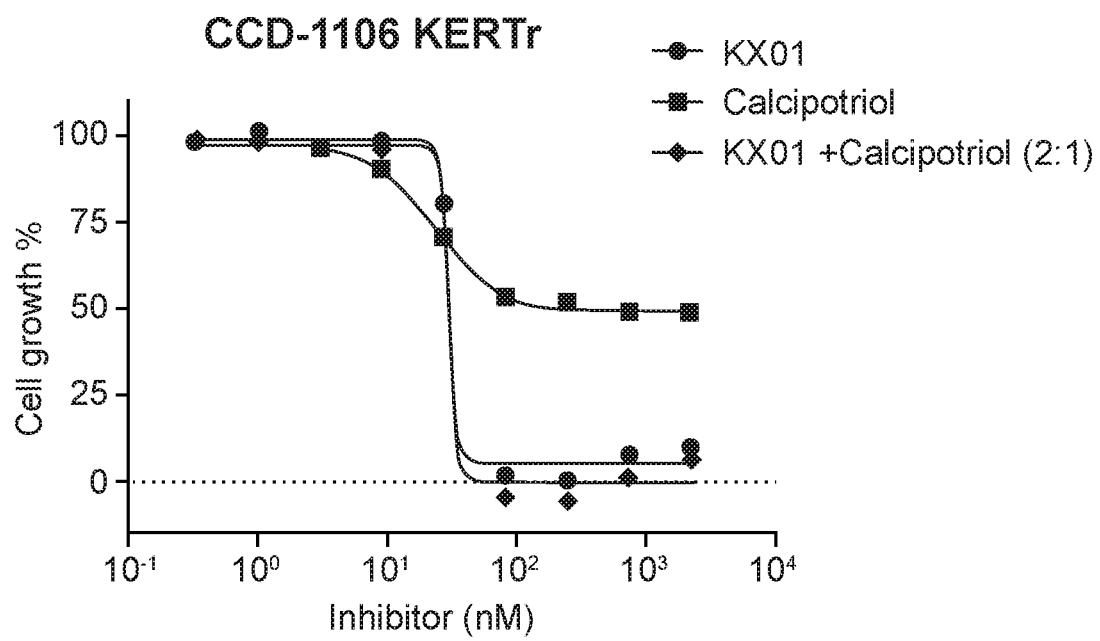
FIG. 3: Results from two experiments comparing cell growth in response to KX01, Calcipotriol, and KX01+calcipotriol at a 2:1 ratio.

Typical data from studies of the effects of compound KX01 provided in combination with calcipotriol on growth of human keratinocytes in culture (cell line CCD-1106 KERTr) are shown in FIGS. 1 to 3 and Tables 1 to 6. FIG. 1 and Tables 1 and 2 show the degree of growth inhibition found in a typical study performed with KX01 and calcipotriol at a 1:5 ratio.

TABLE 1

| nM | Log | KX01 | Calcipotriol | KX01 + Calcipotriol (1:5) |
|---|---|---|---|---|
| 0.333 | −0.47756 | 100.45 | | 96.21622 |
| 1 | 0 | 97.0297 | | 93.33333 |
| 3 | 0.477121 | 90.90909 | 94.0367 | 92.61261 |
| 9 | 0.954243 | 94.68947 | 89.90826 | 88.01802 |
| 27 | 1.431364 | 67.14671 | 70.45872 | 70.27027 |
| 81 | 1.908485 | 1.350135 | 49.3578 | 27.74775 |
| 243 | 2.385606 | 2.070207 | 47.33945 | −2.79279 |
| 729 | 2.862728 | 6.660666 | 46.97248 | −4.32432 |
| 2187 | 3.339849 | 8.910891 | 44.77064 | −1.71171 |
| 6561 | 3.81697 | | 19.17431 | |
| 19683 | 4.294091 | | −9.3578 | |

Table 1 shows the results of cell viability studies comparing cell growth in response to KX01, calcipotriol, and KX01+ calcipotriol at a 1:5 ratio, as graphically depicted in FIG. 1A. Table 2 shows typical $GI_{50}$ and combination index (CI) values for KX01 and calcipotriol (1:5) derived from such studies.

TABLE 2

| | $GI_{50}$ | CI (combination index) |
|---|---|---|
| KX01 | 32 nM | 0.37 |
| Calcipotriol | 265 nM | |
| KX01 + Calcipotriol (1:5) | 43 nM (7.2 nM + 35.8 nM) | |

FIG. 2 shows typical results of similar studies in which KX01 and calcipotriol are used in a 1:2 ratio. Typical numerical data from such a study is shown in Table 3. Table 4 shows typical GI50 and combination index (CI) values for KX01 and calcipotriol (1:2) derived from such studies.

TABLE 3

| nM | Log | KX01 | Calcipotriol | KX01 + Calcipotriol (1:2) |
|---|---|---|---|---|
| 0.333 | −0.47756 | 102.3 | | 100.7 |
| 1 | 0 | 99.9 | | 97.2 |
| 3 | 0.477121 | 100.0 | 95.3 | 95.7 |
| 9 | 0.954243 | 100.2 | 88.8 | 93.8 |
| 27 | 1.431364 | 79.8 | 72.5 | 83.6 |
| 81 | 1.908485 | 4.1 | 53.2 | 20.8 |
| 243 | 2.385606 | 1.2 | 47.7 | −5.4 |
| 729 | 2.862728 | 9.9 | 47.1 | −4.8 |
| 2187 | 3.339849 | 14.9 | 46.7 | 2.5 |
| 6561 | 3.81697 | | 25.2 | |
| 19683 | 4.294091 | | −13.4 | |

TABLE 4

|  | GI$_{50}$ | CI (combination index) |
|---|---|---|
| KX01 | 38 nM | 0.54 |
| Calcipotriol | 310 nM | |
| KX01 + Calcipotriol (1:2) | 49 nM (16.3 nM + 32.7 nM) | |

FIG. 3 shows typical results of studies in which KX01 and calcipotriol are used in a 2:1 ratio. Typical numerical data from such a study is shown in Table 5. Table 6 shows typical GI$_{50}$ and combination index (CI) values for KX01 and calcipotriol (1:5) derived from such studies.

TABLE 5

| nM | Log | KX01 | Calcipotriol | KX01 + Calcipotriol (2:1) |
|---|---|---|---|---|
| 0.333 | −0.47756 | 98.0 | | 98.8 |
| 1 | 0 | 101.3 | | 97.8 |
| 3 | 0.477121 | 96.6 | 96.1 | 96.0 |
| 9 | 0.954243 | 98.2 | 89.7 | 95.3 |
| 27 | 1.431364 | 80.1 | 70.1 | 80.2 |
| 81 | 1.908485 | 1.6 | 52.8 | −4.6 |
| 243 | 2.385606 | −0.1 | 51.0 | −5.9 |
| 729 | 2.862728 | 7.3 | 48.7 | 0.8 |
| 2187 | 3.339849 | 9.5 | 48.3 | 5.8 |
| 6561 | 3.81697 | | 26.5 | |
| 19683 | 4.294091 | | −15.7 | |

TABLE 6

|  | GI$_{50}$ | CI (combination index) |
|---|---|---|
| KX01 | 36 nM | 0.59 |
| Calcipotriol | 339 nM | |
| KX01 + Calcipotriol (2:1) | 30 nM (20 nM + 10 nM) | |

Figure 4:
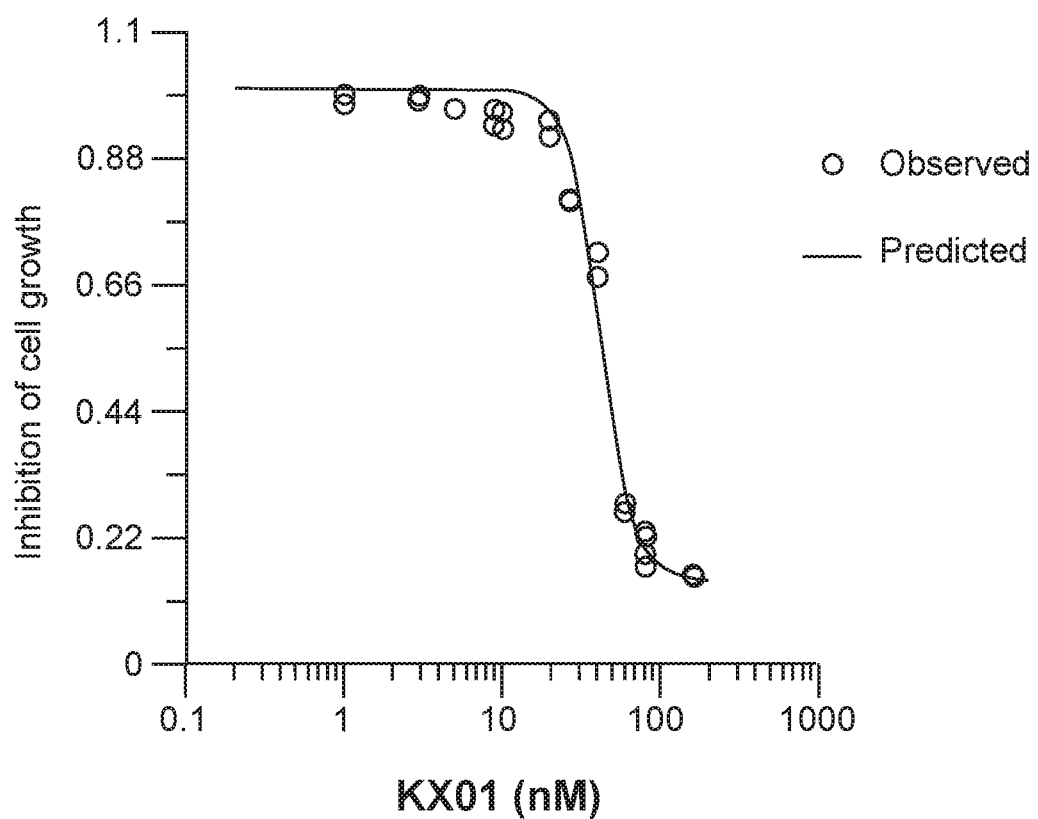
FIG. 4: Inhibition of human keratinocyte growth versus KX01 concentration (treatment duration: 72 hours; cell growth measured using the MTT assay). The $IC_{50}$ of KX01=41.9 nM.
Figure 5:
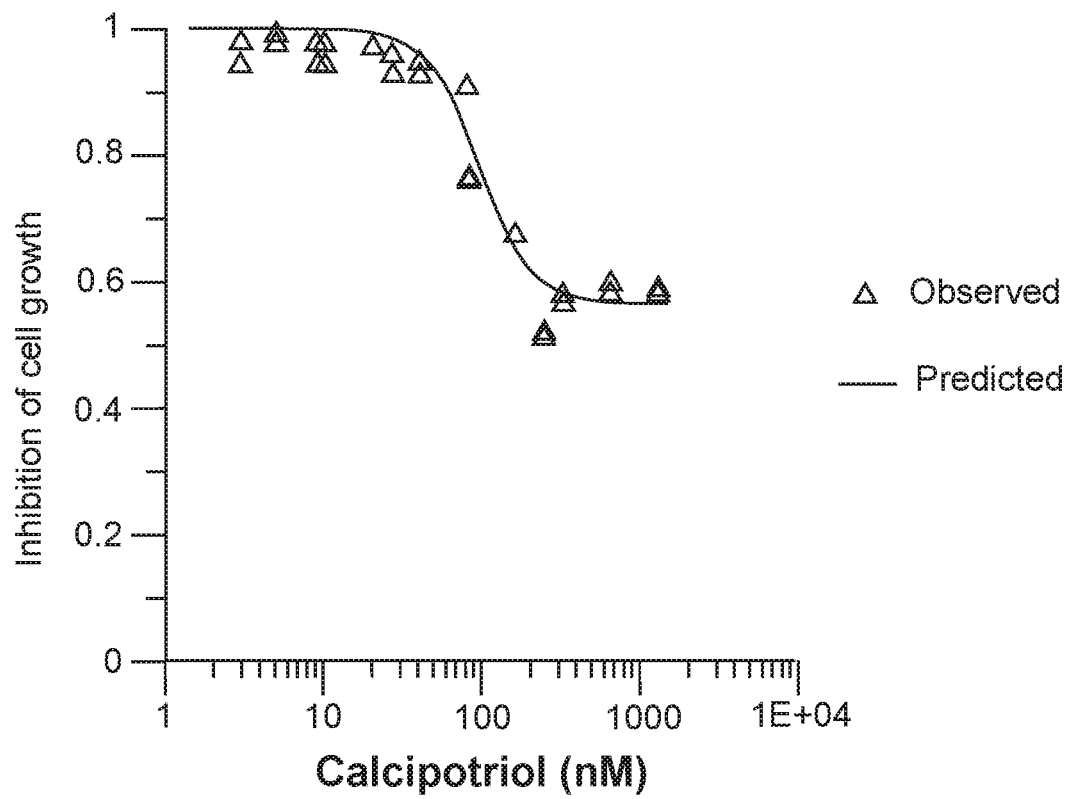
FIG. 5: Inhibition of human keratinocyte growth versus calcipotriol concentration (treatment duration: 72 hours; cell growth measured using the MTT assay). The $IC_{50}$ of calcipotriol=95.5 nM.

In order to determine the range of concentrations over which compounds such as KX01 and calciptriol can inhibit keratinocyte growth and subsequent combinatorial effects, individual dose response curves were determined using a 72 hour exposure to either KX01 or calcipotriol in order to determine individual IC$_{50}$ values. Results are shown in FIG. 4 (which shows typical results for KX01) and FIG. 5 (which shows typical results for calcipotriol). A human keratinocyte cell line was used in these studies. The IC$_{50}$ for KX01 was determined to be 41.9 nM; the IC$_{50}$ for calcipotriol was determined to be 95.5 nM.

Individual dose response curves for KX01 and calcipotriol as determined above can be used to generate dose response surfaces representative of the additive effects of these compounds on keratinocyte growth. Such dose response surfaces can be utilized in detailed combinatorial studies in order to determine if the effects such compounds in combination is antagonistic, merely additive, or showed positive synergistic effects. Synergistic effects can be expressed as "PSI" or Ψ, which has been used as a measure of synergy (see Ariens E J, Van Rossum J M and Simonis A M, Affinity, intrinsic activity and drug interactions, Pharmacol Rev. 1957 Jun. 9(2): 218-36; Chakraborty A and Jusko W J, Pharmacodynamic interaction of recombinant human interleukin-10 and prednisolone using in vitro whole blood lymphocyte proliferation, J. Pharm. Sci. 2002, 91: 1334). A PSI value of 1 corresponds to an additive effect. A PSI value of less than 1 indicates a synergistic effect, and a PSI value of greater than 1 indicates an antagonistic effect.

Figure 6:
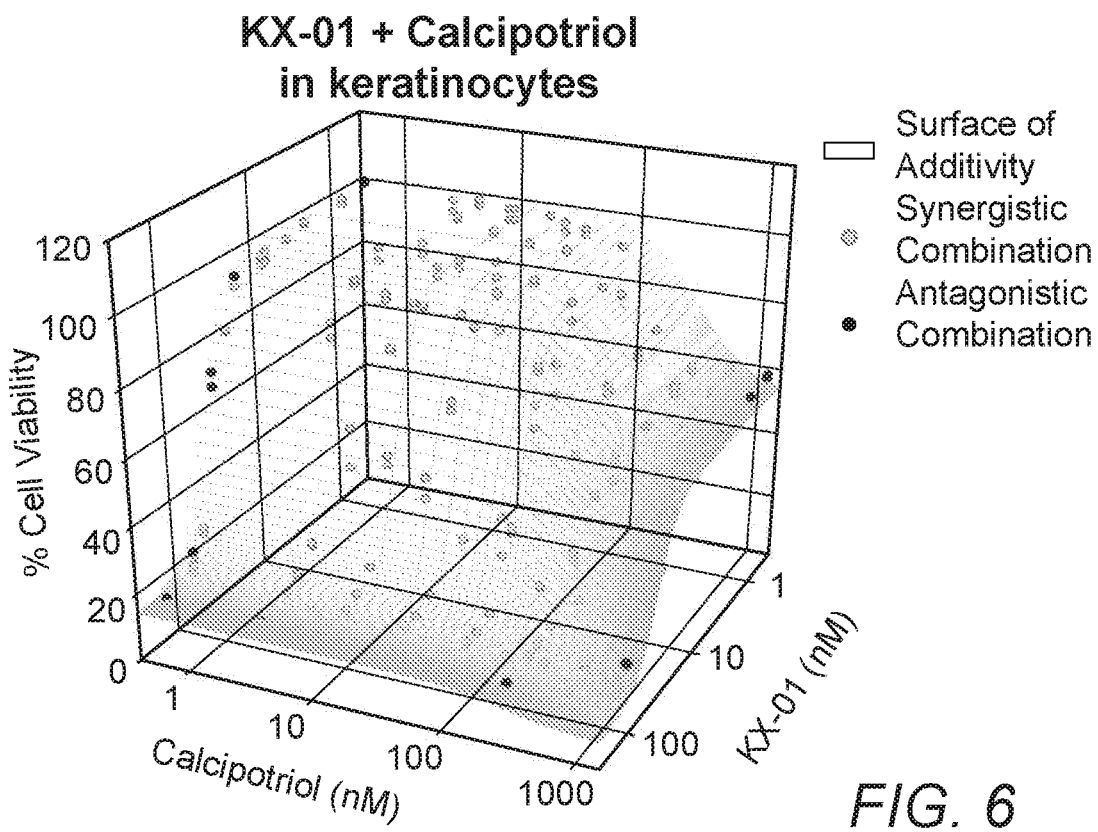
FIG. 6: Dose response surface of cell viability versus calcipotriol concentration versus KX01 concentration. Synergistic combinations of calcipotriol and KX01 are below the surface of additivity (indicating enhanced inhibition of growth), and antagonistic combinations are above the surface of additivity (indicative of reduced inhibition of growth).

Cell viability was measured in a number of experiments. In Experiment 1, the concentrations of calcipotriol were: 0, 3, 9, 27, 81, and 243 nM, and the concentrations of KX01 were: 0, 5, 10, 20, 40, 60, 80, and 160 nM. In Experiment 2, the concentrations of calcipotriol were: 0, 5, 10, 20, 40, 80, 160, 320, and 1280 nM, and the concentrations of KX01 were: 1, 3, 9, 27, and 81 nM. The results are shown in FIG. 6, which shows the calculated additive response surface derived from individual dose response curves for each compound and individual data points representing the results of individual combinations. Synergistic effects are indicated when the observed response lies below the additive response surface; antagonistic effects are indicated when the observed response lies above the additive response surface. It is notable that unexpected synergy is observed across a range of concentrations and combinations.

Tables 7, 8, and 9 show the results for determination of individual IC$_{50}$ and maximum inhibitory concentration values for KX01 and calcipotriol, as well as the PSI value for the drug combination. Table 7 shows values derived from the study depicted in FIG. 6. Tables 8 and 9 show values derived from subsequent replicate studies.

TABLE 7

| Parameters | Estimate (CV %) |
|---|---|
| PSI | 0.571 (3.72) |
| Max Inhibition KX01 | 0.856 (1.31) |
| IC$_{50}$ KX01 | 41.3 (3.62) |
| Max Inhibition Calcipotriol | 0.474 (2.74) |
| IC$_{50}$ Calcipotriol | 112 (7.01) |

TABLE 8

| Parameters | Estimate (CV %) |
|---|---|
| PSI | 0.626 (3.26) |
| Max Inhibition KX01 | 0.77 (2.11) |
| IC$_{50}$ KX01 | 32.8 (6.29) |
| Max Inhibition Calcipotriol | 0.36 (3.00) |
| IC$_{50}$ Calcipotriol | 59.3 (10.4) |

TABLE 9

| Parameters | Estimate (CV %) |
|---|---|
| PSI | 0.787 (4.99) |
| Max Inhibition KX01 | 0.741 (5.21) |
| IC$_{50}$ KX01 | 47.0 (14.8) |
| Max Inhibition Calcipotriol | 0.439 (4.99) |
| IC$_{50}$ Calcipotriol | 112 (5.72) |

As shown above, a significant synergistic effect in inhibition of keratinocyte growth is consistently found when KX01 and calcipotriol are used in combination. In some embodiments such synergy is observed when the concentration of KX01 is about 1 to about 30 nM and the concentration of calcipotriol is about 3 to about 300 nM, and is present when KX01 (or a related compound) and calcipotriol (or a similar vitamin D derivative) are provided in a suitable formulation in amounts sufficient to generate such concentrations in the tissue to be treated. Such formulation can provide KX01 (or a similar compound) and calcipotriol (or a similar vitamin D derivative) in amounts that provide a ratio of these active compounds that in turn provides a synergistic effect in regards to inhibition of keratinocyte growth.

Figure 7:
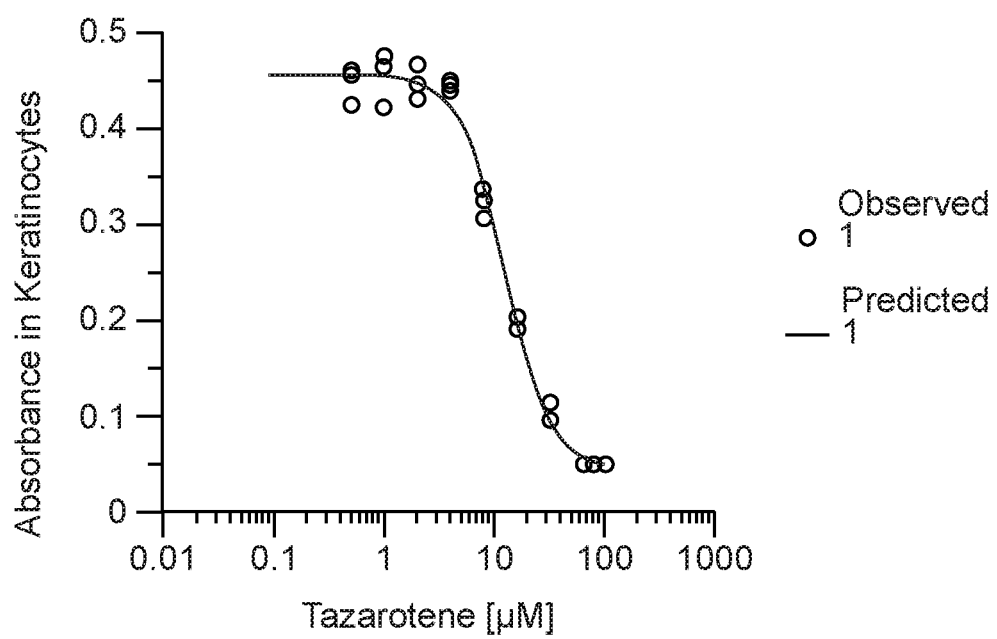
FIG. 7: Inhibition of CCD1106 KERTr keratinocyte growth by tazarotene, as determined by staining.
Figure 8:
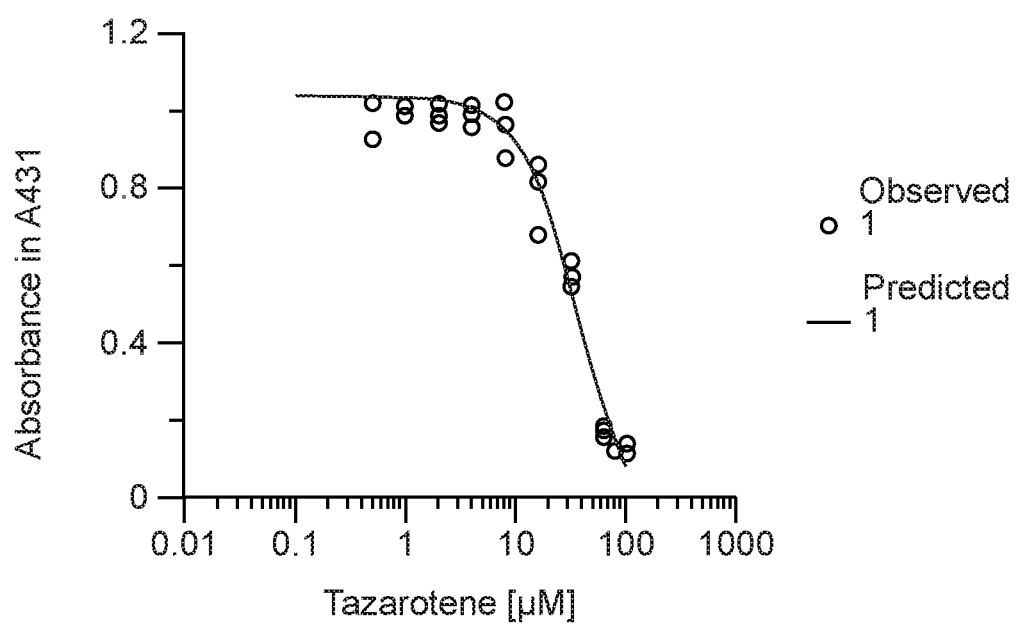
FIG. 8: Inhibition of A431 cell growth by tazarotenee, as determined by staining.

Inventors have also found that treatment with KX01 can be combined with a retinoid and/or retinoid analog to provide a synergistic (i.e. greater than additive) effect in the inhibition of cell proliferation/growth that is characteristic of hyperproliferative disorders. Examples of suitable retinoids include retinol, retinal, retinoic acid isotretinoin, alitreninoin, etretinate, acitretin, adapalene, bexarotene, and/or tazarotene. FIGS. 7 and 8 show the effects of tazarotene on growth of cells in culture, including CCD-1106 KERTr keratinocytes (FIG. 7) and A431 cells (epidermoid cells obtained from a human squamous cell carcinoma, FIG. 8). Numerical data from these studies is provided in Table 10, which shows data derived from CCD-1106 KERTr keratinocytes and from A431 cells.

TABLE 10

| Parameter | Estimate (CV %) (Keratinocytes) | Estimate (CV %) (A431) |
|---|---|---|
| R0 | 0.455 (1.07) | 1.03 (1.94) |
| Maximum inhibition | 0.903 (1.68) | 1.09 (12.3) |
| IC$_{50}$ | 12.4 (4.12) | 36.3 (19.8) |
| H | 2.11 (7.93) | 1.66 (19.9) |

Studies on the effects of combined treatment with KX01 and tazarotene were performed, and showed a clear and unexpected synergistic effect. Typical results are shown in Table 11.

TABLE 11

| | KX01 (nM) | Tazarotene (nM) |
|---|---|---|
| IC$_{50}$ | 45 | 13.3 µM |
| Imax | 0.92 | 1.1 |
| H | 3.3 | 1.0 |

| PSI value | 95% Confidence Interval |
|---|---|
| 0.76 (3.3% CV) | 0.7-0.8 |

In addition to growth inhibition, Inventors also investigated the effect of KX01 on apoptosis in keratinocytes. CCD-1106 KERTr cells (1×10$^6$) were seeded in 60 mm dishes and treated with test compounds at varying concentrations (e.g. KX01: 20 to 500 nM; calcipotriol 50 to 1000 nM) for 24 hours. Cell apoptosis was assessed by using a FITC annexin V apoptosis detection kit (BD Biosciences™) according to manufacturer's instruction. Briefly, cells were collected in 1× binding buffer and incubated with fluorescein isothiocyanate (FITC)-conjugated annexin V and propidium iodide (PI) for 15 minutes at room temperature in the dark, followed by flow cytometry analysis using a LSRFortessa™ flow cytometer (BD Biosciences™). Results are summarized in Table 12, which shows the percentage of late apoptic cells identified for various KX01 and calcipitriol combinations.

TABLE 12

| [Calcipotriol], nM | | | | | |
|---|---|---|---|---|---|
| 1,000 | 4.19 | 3.15 | 4.61 | 8.74 | 4.64 |
| 500 | 4.13 | 2.71 | 4.88 | 7.93 | 5.89 |
| 200 | 2.06 | 2.55 | 4.97 | 7.94 | 6.13 |
| 50 | 2.41 | 2.12 | 4.50 | 5.70 | 5.36 |
| 0 | 2.08 | 2.09 | 3.50 | 6.33 | 4.34 |
| | 0 | 20 | 40 | 100 | 500 [KX01], nM |

Synergy between KX01 and calcipotriol in regards to increasing the number of keratinocytes undergoing apoptosis is evident. For example the effect of 200 nm calcipotriol is not distinguishable from that of control cells receiving no drug treatment, however the same concentration of calcipotriol enhances the effect of KX01 by approximately 40%.

The inventive subject matter also includes using blue light (e.g. 280 nm to 500 nm), UV/A light, and/or UV/B light to illuminate skin during, prior to, or following treatment with KX01 (either alone or in combination with other compounds), particularly where synergistic effects permit reduction in blue light exposure and/or drug dosage relative to either light exposure or chemotherapy alone. Any suitable source of blue light can be used. Suitable sources of blue light include incandescent bulbs, fluorescent lights, LED light sources, and laser light sources. Such a light source can be a broad spectrum light sources (i.e. providing a range of wavelengths exceeding 20 nm in width) or a narrow spectrum light source (i.e. providing a range of wavelengths spanning 20 nm or less). In some embodiments the light source can produce primarily (i.e. >90%) blue light. In other embodiments the light source can produce both blue, and non-blue light, with non-blue light selectively blocked by an optical filter. In a preferred embodiment the light source for visible blue light is a panel or fluorescent light emitting a narrow bandwidth light centered at 460 nm. In another preferred embodiment the light sources for UVB light is a fluorescent and/or LED/LCD panel light emitting a narrow bandwidth centered at 311 nm.

Figure 9:
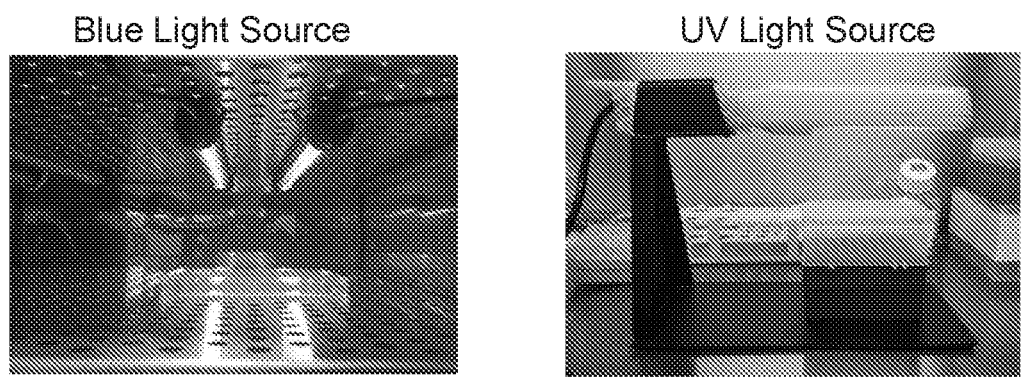
FIG. 9: Results of exposure of keratinocytes to a light source providing primarily visible blue light (top left) or to a light source providing primarily UVB light (top right).
Figure 9:
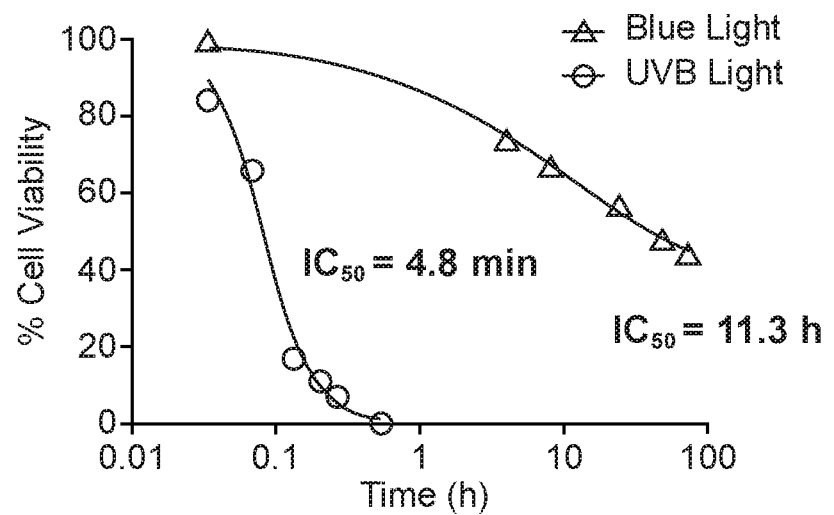
Figure 10:
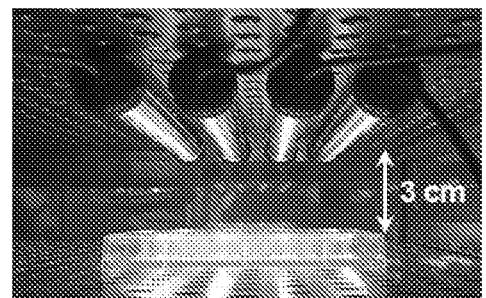
FIG. 10: Improved reduction in viability of keratinocytes at increased blue light intensity.
Figure 10:
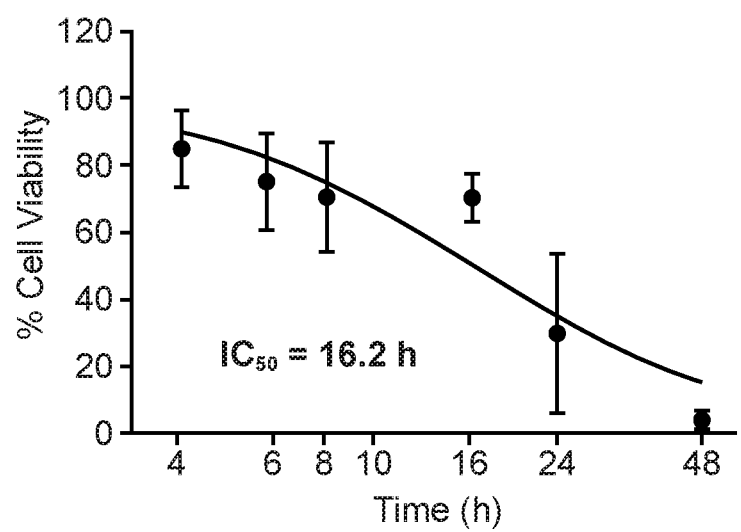

It should be appreciated that exposure to blue light alone can reduce cell viability, and that different sources of blue light can provide different effects. An example of this is provided in FIG. 9, which shows the results of exposure of CCD 1106 KERTr human keratinocytes cells to different blue light sources (i.e. blue visible light or UVB) for 72 hours. It is apparent that UVB light is significantly more effective in reducing keratinocyte viability relative to visible blue light, although both are effective. As shown in FIG. 10, the overall effectiveness (in terms of absolute reduction in cell viability) of light sources providing primarily visible blue light can be improved by increasing its intensity.

The effects of combined treatment with KX01, a vitamin D derivative, and/or blue/UV light exposure were characterized using a cell proliferation assay. Cell proliferation was assessed by using an MTT assay. Cells were seeded in 96-well plate (3,000-5,000 cells per well) and treated with test compounds at varying concentrations (e.g. KX01: 5 to 80 nM; calcipotriol 5 to 1,280 nM) for 72 hours, either in the dark or exposed to blue light irradiation (for 2, 4, or 6 hours). To each well, 10 µl of 3-(4,5-dimethylthiazol-2-yl)-2,5-diphenyltetrazolium bromide (MTT) (RPI Corporation™) solution (5 mg/ml in PBS) was added and incubated at 37° C. for 3 hours. Next, 100 µl of 20% SDS was added to each well. After overnight incubation at 37° C., the absorbance in each well was measured at 570 nm in a microplate reader (Molecular Devices™). The cell growth curve and $GI_{50}$s were calculate using GraphPad Prism™ 5 software.

Tables 13 and 14 show the results of cell growth inhibition studies (expressed as a percentage relative to control cell growth) for treatment with either KX01 or calcipotriol in combination with exposure to blue light.

TABLE 13

| Blue light (hours) | | | | | | |
|---|---|---|---|---|---|---|
| 6 | 50 | 56 | 70 | 88 | 87 | |
| 4 | 41 | 47 | 64 | 87 | 92 | |
| 2 | 26 | 27 | 63 | 92 | 97 | |
| 0 | 0 | 4 | 40 | 90 | 96 | |
|   | 0 | 10 | 20 | 40 | 80 | [KX01], nM |

Table 13 shows the results of a cell proliferation assay performed using KX01 and blue light and the CCD 1106 KERTr human keratinocyte cell line. The percentage of growth inhibition relative to untreated control is shown.

TABLE 14

| Blue light (hours) | | | | | | |
|---|---|---|---|---|---|---|
| 6 | 53 | 56 | 59 | 71 | 72 | 66 |
| 4 | 48 | 53 | 58 | 70 | 71 | 69 |
| 2 | 25 | 32 | 39 | 55 | 66 | 62 |
| 0 | 0 | 9 | 24 | 45 | 48 | 43 |
|   | 0 | 5 | 20 | 80 | 320 | 1,280 [calcipotriol], nM |

Table 14 shows the results of a cell proliferation assay performed using calcipotriol and blue light and the CCD 1106 KERTr human keratinocyte cell line. The percentage of growth inhibition relative to untreated control is shown.

Tables 15 to 18 show the effects of combined treatment with KX01, calcipotriol, and exposure to blue light at 0 hours, 2 hours, 4 hours, and 6 hours of light exposure (respectively). Values are expressed as the percentage of growth inhibition relative to cells grown under control conditions (0 hours blue light, [KX01]=0, [calcipotriol]=0). It should be appreciated that synergy (i.e. greater than additive) effects between blue light exposure and combined KX01 and calcipotriol treatment are observed, for example at 2 hours of blue light exposure and combined treatment with 10 nM KX01 and 20 nM calcipotriol.

TABLE 15

| [Calcipotriol], nM | | | | | | |
|---|---|---|---|---|---|---|
| 1,280 | 43 | 60 | 86 | 95 | 98 | |
| 320 | 48 | 69 | 90 | 100 | 100 | |
| 80 | 45 | 67 | 89 | 100 | 100 | |
| 20 | 24 | 48 | 85 | 100 | 100 | |
| 5 | 9 | 22 | 80 | 100 | 100 | |
| 0 | 0 | 9 | 24 | 45 | 48 | |
|   | 0 | 10 | 20 | 40 | 80 | [KX01], nM |

TABLE 16

| [Calcipotriol], nM | | | | | | |
|---|---|---|---|---|---|---|
| 1,280 | 62 | 79 | 91 | 95 | 100 | |
| 320 | 66 | 86 | 96 | 100 | 100 | |
| 80 | 55 | 84 | 96 | 100 | 100 | |
| 20 | 39 | 76 | 97 | 100 | 100 | |
| 5 | 32 | 47 | 92 | 100 | 100 | |
| 0 | 25 | 32 | 74 | 98 | 48 | |
|   | 0 | 10 | 20 | 40 | 80 | [KX01], nM |

TABLE 17

| [Calcipotriol], nM | | | | | | |
|---|---|---|---|---|---|---|
| 1,280 | 69 | 81 | 91 | 96 | 97 | |
| 320 | 71 | 85 | 93 | 99 | 100 | |
| 80 | 70 | 83 | 90 | 100 | 100 | |
| 20 | 58 | 69 | 86 | 98 | 99 | |
| 5 | 53 | 62 | 78 | 94 | 94 | |
| 0 | 48 | 56 | 69 | 92 | 93 | |
|   | 0 | 10 | 20 | 40 | 80 | [KX01], nM |

TABLE 18

| [Calcipotriol], nM | | | | | | |
|---|---|---|---|---|---|---|
| 1,280 | 66 | 80 | 91 | 97 | 99 | |
| 320 | 72 | 82 | 91 | 97 | 98 | |
| 80 | 71 | 82 | 88 | 95 | 97 | |
| 20 | 59 | 72 | 82 | 93 | 93 | |
| 5 | 56 | 67 | 75 | 88 | 87 | |
| 0 | 53 | 62 | 67 | 84 | 83 | |
|   | 0 | 10 | 20 | 40 | 80 | [KX01], nM |

Similar studies were performed using a squamous cell carcinoma cell line (SCC A431). Tables 19 and 20 show the results of cell growth inhibition studies (expressed as a percentage relative to control cell growth) for treatment with either KX01 or calcipotriol in combination with exposure to blue light.

TABLE 19

| Blue light (hours) | | | | | | |
|---|---|---|---|---|---|---|
| 6 | 66 | 79 | 81 | 81 | 82 | |
| 4 | 45 | 66 | 76 | 73 | 75 | |
| 2 | 40 | 40 | 97 | 97 | 95 | |
| 0 | 0 | 0 | 99 | 99 | 99 | |
|   | 0 | 10 | 20 | 40 | 80 | [KX01], nM |

Table 19 shows the results of a cell proliferation assay performed using KX01 and blue light and a squamous cell human carcinoma cell line (SCC A431). The percentage of growth inhibition relative to untreated control is shown.

TABLE 20

| Blue light (hours) | | | | | | |
|---|---|---|---|---|---|---|
| 6 | 66 | 67 | 69 | 67 | 67 | 68 |
| 4 | 45 | 49 | 44 | 47 | 49 | 43 |

TABLE 20-continued

Blue light (hours)

| 2 | 18 | 26 | 36 | 41 | 35 | 38 |
| 0 | 0 | 19 | 30 | 40 | 41 | 36 |
|  | 0 | 5 | 20 | 80 | 320 | 1,280 | [calcipotriol], nM |

Tables 21 to 24 show the effects of combined treatment with KX01, calcipotriol, and exposure to blue light at 0 hours, 2 hours, 4 hours, and 6 hours of light exposure (respectively) on human squamous cell carcinoma cells. Values are expressed as the percentage of growth inhibition relative to cells grown under control conditions (0 hours blue light, [KX01]=0, [calcipotriol]=0). The percentage of growth inhibition relative to an untreated control is shown. It should be appreciated that synergy (i.e. greater than additive) effects between blue light exposure and combined KX01 and calcipotriol treatment are observed, for example at 2 to 6 hours of blue light exposure and combined treatment with 10 nM KX01 and 5 nM calcipotriol, and at 2 hours of exposure to blue light and combined treatment with 10 nM KX01 and from 5 to 1,280 nM calcipotriol.

TABLE 21

[Calcipotriol], nM

| 1,280 | 36 | 31 | 75 | 96 | 100 |
| 320 | 41 | 26 | 74 | 98 | 99 |
| 80 | 40 | 29 | 75 | 97 | 100 |
| 20 | 30 | 26 | 76 | 96 | 100 |
| 5 | 19 | 1 | 77 | 96 | 100 |
| 0 | 0 | 0 | 80 | 99 | 99 |
|  | 0 | 10 | 20 | 40 | 80 | [KX01], nM |

TABLE 22

[Calcipotriol], nM

| 1,280 | 38 | 55 | 78 | 95 | 98 |
| 320 | 35 | 56 | 79 | 96 | 98 |
| 80 | 41 | 56 | 80 | 97 | 98 |
| 20 | 39 | 52 | 80 | 98 | 98 |
| 5 | 26 | 46 | 78 | 96 | 98 |
| 0 | 18 | 40 | 79 | 97 | 95 |
|  | 0 | 10 | 20 | 40 | 80 | [KX01], nM |

TABLE 23

[Calcipotriol], nM

| 1,280 | 43 | 69 | 75 | 77 | 82 |
| 320 | 49 | 72 | 77 | 79 | 83 |
| 80 | 47 | 72 | 78 | 80 | 83 |
| 20 | 44 | 68 | 74 | 78 | 82 |
| 5 | 49 | 68 | 74 | 76 | 80 |
| 0 | 45 | 66 | 69 | 73 | 75 |
|  | 0 | 10 | 20 | 40 | 80 | [KX01], nM |

TABLE 24

[Calcipotriol], nM

| 1,280 | 68 | 73 | 88 | 93 | 94 |
| 320 | 67 | 79 | 88 | 91 | 96 |
| 80 | 67 | 81 | 88 | 89 | 91 |
| 20 | 69 | 81 | 86 | 88 | 88 |
| 5 | 67 | 79 | 79 | 84 | 86 |
| 0 | 66 | 79 | 81 | 81 | 82 |
|  | 0 | 10 | 20 | 40 | 80 | [KX01], nM |

As shown, KX01 and calcipotriol in combination exhibit synergistic inhibition of cell growth in keratinocytes in vitro, for example within the range of 1 to 30 nM KX01 and 3 to 300 nM calcipotriol. Without wishing to be bound by theory, evidence suggests that at least part of this apparent growth inhibition is due to induction of apoptosis by KX01 and calcipotriol. In addition, blue light shows additive effect on cell growth inhibition in keratinocytes in vitro that are exposed to KX01, calcipotriol, and/or a combination of KX01 and calcipotriol, indicating that controlled exposure to blue light can serve as a valuable adjunct to chemotherapies.

Additional studies were performed to evaluate potential synergistic effects of cell growth inhibition of human keratinocytes on exposure to blue light and to KX01 or calcipotriol. Results are shown below in Table 25 and Table 26.

TABLE 25

Blue light (hours)

| 6 | 47 | 57 | 73 | 88 | 88 |
| 4 | 44 | 50 | 68 | 86 | 90 |
| 2 | 29 | 34 | 68 | 91 | 96 |
| 0 | 0 | 6 | 49 | 90 | 95 |
|  | 0 | 10 | 20 | 40 | 80 | [KX01], nM |

TABLE 26

Blue light (hours)

| 6 | 47 | 51 | 58 | 67 | 72 | 67 |
| 4 | 44 | 47 | 52 | 64 | 67 | 63 |
| 2 | 29 | 33 | 39 | 53 | 60 | 58 |
| 0 | 0 | 6 | 17 | 35 | 48 | 37 |
|  | 0 | 5 | 20 | 80 | 320 | 1,280 | [calcipotriol], nM |

Synergistic effects between blue light exposure and KX01 or calcipotriol on cell growth inhibition in human keratinocytes were observed. For example, synergy is evident at 6 hours of blue light exposure in combination with 10 nm KX01.

Studies were also performed to evaluate potential synergistic effects of cell growth inhibition of human keratinocytes on exposure to blue light and to KX01 in combination with calcipotriol. Results are shown below in Tables 27 to Table 30, which show results from 0, 2, 4, and 6 hours of blue light exposure (respectively). Values are expressed as the percentage of growth inhibition relative to cells grown under control conditions (0 hours blue light, [KX01]=0, [calcipotriol]=0). It should be appreciated that synergy (i.e. greater than additive) effects between blue light exposure and combined KX01 and calcipotriol treatment are observed, and that the synergistic effect observed at 2 hours of blue light exposure and combined treatment with 10 nM KX01 and 20 nM calcipotriol is confirmed.

TABLE 27

| [Calcipotriol], nM | | | | | | |
|---|---|---|---|---|---|---|
| 1,280 | 37 | 56 | 85 | 93 | 95 | |
| 320 | 48 | 65 | 91 | 98 | 98 | |
| 80 | 35 | 57 | 91 | 98 | 98 | |
| 20 | 17 | 30 | 86 | 97 | 97 | |
| 5 | 6 | 13 | 72 | 95 | 97 | |
| 0 | 0 | 6 | 49 | 90 | 95 | |
| | 0 | 10 | 20 | 40 | 80 | [KX01], nM |

TABLE 28

| [Calcipotriol], nM | | | | | | |
|---|---|---|---|---|---|---|
| 1,280 | 58 | 76 | 91 | 96 | 99 | |
| 320 | 60 | 83 | 97 | 100 | 100 | |
| 80 | 53 | 79 | 97 | 100 | 100 | |
| 20 | 39 | 63 | 91 | 99 | 100 | |
| 5 | 33 | 42 | 83 | 97 | 99 | |
| 0 | 29 | 34 | 68 | 91 | 96 | |
| | 0 | 10 | 20 | 40 | 80 | [KX01], nM |

TABLE 29

| [Calcipotriol], nM | | | | | | |
|---|---|---|---|---|---|---|
| 1,280 | 63 | 76 | 90 | 95 | 96 | |
| 320 | 67 | 80 | 94 | 98 | 98 | |
| 80 | 64 | 76 | 90 | 98 | 98 | |
| 20 | 52 | 61 | 82 | 93 | 97 | |
| 5 | 47 | 54 | 74 | 90 | 94 | |
| 0 | 44 | 50 | 68 | 86 | 90 | |
| | 0 | 10 | 20 | 40 | 80 | [KX01], nM |

TABLE 30

| [Calcipotriol], nM | | | | | | |
|---|---|---|---|---|---|---|
| 1,280 | 67 | 79 | 90 | 95 | 96 | |
| 320 | 72 | 81 | 93 | 96 | 97 | |
| 80 | 67 | 78 | 90 | 95 | 97 | |
| 20 | 58 | 68 | 84 | 93 | 94 | |
| 5 | 51 | 61 | 80 | 92 | 91 | |
| 0 | 47 | 57 | 73 | 88 | 88 | |
| | 0 | 10 | 20 | 40 | 80 | [KX01], nM |

Similar studies were performed to determine the synergistic effects on cell growth inhibition of squamous cell carcinoma cells (SCC A431) on exposure to blue light and KX01 or calcipotriol. Results are shown below in Tables 31 and 32, which show results for KX01 and calcipotriol (respectively). Values are expressed as the percentage of growth inhibition relative to cells grown under control conditions (0 hours blue light, [KX01]=0, [calcipotriol]=0).

TABLE 31

| Blue light (hours) | | | | | | |
|---|---|---|---|---|---|---|
| 6 | 65 | 77 | 83 | 86 | 88 | |
| 4 | 48 | 66 | 74 | 80 | 84 | |
| 2 | 23 | 44 | 83 | 99 | 98 | |
| 0 | 0 | 11 | 79 | 100 | 99 | |
| | 0 | 10 | 20 | 40 | 80 | [KX01], nM |

TABLE 32

| Blue light (hours) | | | | | | |
|---|---|---|---|---|---|---|
| 6 | 65 | 62 | 63 | 61 | 60 | 58 |
| 4 | 48 | 50 | 48 | 50 | 51 | 48 |
| 2 | 23 | 27 | 36 | 40 | 37 | 39 |
| 0 | 0 | 14 | 19 | 27 | 31 | 28 |
| | 0 | 5 | 20 | 80 | 320 | 1,280 | [calcipotriol], nM |

Synergistic effects between blue light exposure and KX01 on cell growth inhibition in squamous cell carcinoma cells are evident, for example at 10 nM KX01.

Studies were also performed to evaluate potential synergistic effects of cell growth inhibition of human squamous cell carcinoma cells on exposure to blue light and to KX01 in combination with calcipotriol. Results are shown below in Tables 33 to Table 36, which show results from 0, 2, 4, and 6 hours of blue light exposure (respectively). Values are expressed as the percentage of growth inhibition relative to cells grown under control conditions (0 hours blue light, [KX01]=0, [calcipotriol]=0). It should be appreciated that synergy (i.e. greater than additive) effects between blue light exposure and combined KX01 and calcipotriol treatment are observed, for example at 2 to 6 hours of blue light exposure and combined treatment with 10 nM KX01 and 5 nM calcipotriol, and at 2 hours of exposure to blue light and combined treatment with 10 nM KX01 and from 5 to 1,280 nM calcipotriol are confirmed.

TABLE 33

| [Calcipotriol], nM | | | | | | |
|---|---|---|---|---|---|---|
| 1,280 | 28 | 29 | 70 | 97 | 100 | |
| 320 | 31 | 29 | 69 | 97 | 99 | |
| 80 | 26 | 28 | 70 | 97 | 100 | |
| 20 | 19 | 23 | 72 | 97 | 100 | |
| 5 | 14 | 10 | 74 | 97 | 100 | |
| 0 | 0 | 11 | 79 | 100 | 99 | |
| | 0 | 10 | 20 | 40 | 80 | [KX01], nM |

TABLE 34

| [Calcipotriol], nM | | | | | | |
|---|---|---|---|---|---|---|
| 1,280 | 39 | 57 | 79 | 96 | 98 | |
| 320 | 37 | 56 | 78 | 97 | 98 | |
| 80 | 40 | 55 | 79 | 98 | 99 | |
| 20 | 36 | 51 | 81 | 99 | 99 | |
| 5 | 27 | 45 | 81 | 98 | 99 | |
| 0 | 23 | 44 | 83 | 99 | 98 | |
| | 0 | 10 | 20 | 40 | 80 | [KX01], nM |

TABLE 35

| [Calcipotriol], nM | | | | | | |
|---|---|---|---|---|---|---|
| 1,280 | 48 | 66 | 74 | 81 | 88 | |
| 320 | 51 | 67 | 76 | 81 | 87 | |
| 80 | 50 | 67 | 76 | 81 | 88 | |
| 20 | 48 | 66 | 74 | 81 | 87 | |
| 5 | 49 | 66 | 76 | 81 | 87 | |
| 0 | 48 | 66 | 74 | 80 | 84 | |
| | 0 | 10 | 20 | 40 | 80 | [KX01], nM |

TABLE 36

| [Calcipotriol], nM | | | | | | |
|---|---|---|---|---|---|---|
| 1,280 | 57 | 70 | 89 | 96 | 96 | |
| 320 | 60 | 74 | 89 | 94 | 95 | |
| 80 | 61 | 75 | 88 | 92 | 94 | |
| 20 | 63 | 76 | 87 | 91 | 93 | |
| 5 | 62 | 75 | 83 | 89 | 91 | |
| 0 | 65 | 77 | 83 | 86 | 88 | |
| | 0 | 10 | 20 | 40 | 80 | [KX01], nM |

Figure 11:
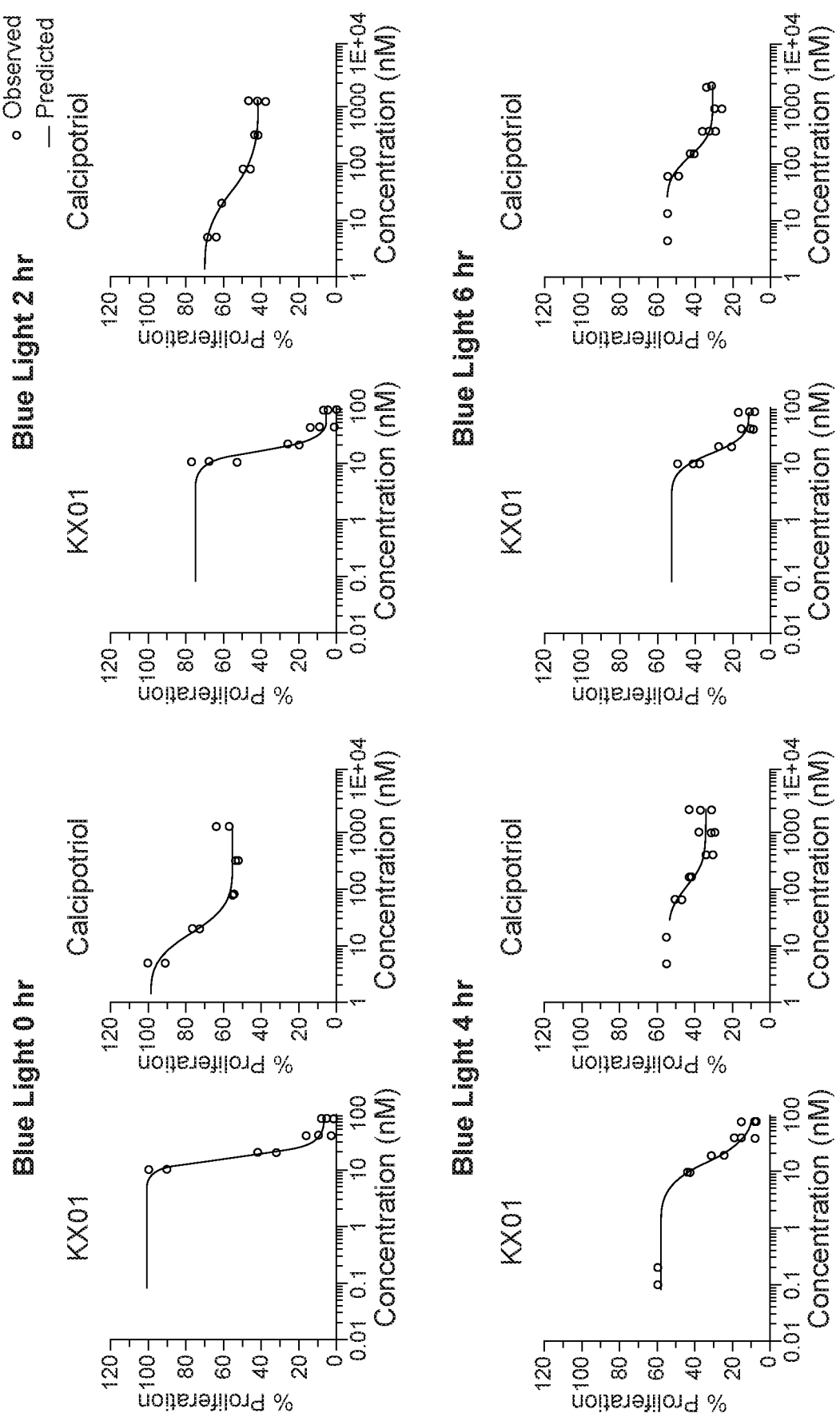
FIG. 11: Effects of blue light exposure in combination with either KX01 or calcipotriol for from 0 hours (no blue light exposure) to 6 hours on keratinocyte proliferation.
Figure 12:
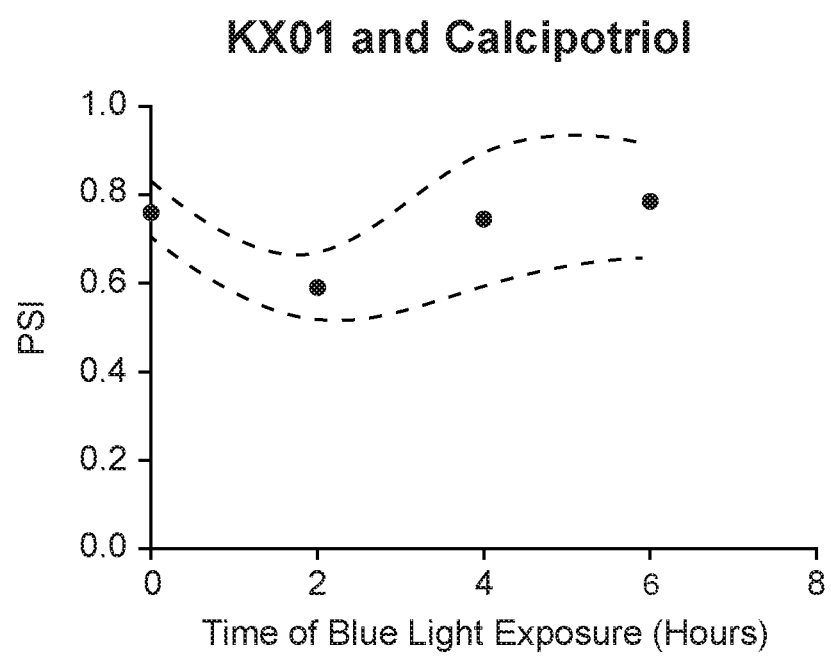
FIG. 12: PSI values determined for combined effects of treatment with blue light, KX01, and/or calcipotriol on skin cell proliferation.

Additional studies were performed to determine PSI values for the inhibition of skin cell proliferation by blue light exposure in combination with KX01 and/or calcipotriol exposure. FIG. 11 shows results of keratinocyte cell proliferation on exposure to either KX01 or calcipotriol at various concentrations and exposure to blue light for from 0 to 6 hours. FIG. 12 shows the results of calculations of PSI values for combined treatment with KX01, calcipotriol, and blue light exposure, where a value of less than 1 indicates a synergistic effect. Synergy between KX01 and calcipotriol is evident in the absence of blue light (0 hours), but additional synergy (as indicated by a further reduced psi value) is seen on exposure to blue light with this drug combination. This is particularly evident at 2 hours of blue light exposure. Table 37 provides a summary of the numeric data presented in FIG. 12.

TABLE 37

| Time (hours) | PSI (95% confidence interval) |
|---|---|
| 0 | 0.762 (0.696-0.828) |
| 2 | 0.591 (0.514-0.668) |
| 4 | 0.746 (0.595-0.897) |
| 6 | 0.786 (0.660-0.913) |

Inventors believe that additional synergistic effects between exposure to blue light and KX01 and/or calcipotriol can be realized through optimization of the wavelength of blue light utilized, spectral range of the blue light utilized, and/or light intensity.

The inventive compositions and methods can treat dermatological hyperproliferative conditions, including malignant or benign hyperproliferative disorders. Malignant hyperproliferative epidermal pathologies include: squamous-cell carcinoma (SCC), basal-cell carcinoma (BCC) and other non-melanoma skin cancers (NMSCs). Benign hyperproliferative epidermal pathologies include psoriasis, other disturbances of keratinization, common warts, keratoacanthoma, seborrhoeic keratosis, seborrhea and ichthyosis. Contemplated conditions that may be treated using compositions and method according to the inventive subject matter includes: solar keratosis, ichthyosis, Grover's disease, common warts, keratoacanthoma, seborrhoeic keratosis, scleroderma, seborrhea, HIV-associated dermatoses, hyperproliferation associated with wound healing, chronic dermatoses of autoimmune type (e.g., scleroderma and pemphigus vulgaris), alopecia, skin atrophy, photoageing, keratodermos, acne vulgaris, acne rosacea, lichen planus, cutaneous lupus erythematosus, pre-malignant conditions (e.g., melanocytic naevus, myelodysplastic syndrome, among others), Darriers disease, palmoplanter keratodermas, *Pityriasis rubra* pilaris, epidermal naevoid syndromes, erythrokeratoderma variabilis, epidermolytic hyperkeratoses, non-bullous ichthyosiform erythroderma, cutaneous lupus erythematosus, and lichen planus.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating actinic keratosis in a subject in need thereof, the method comprising:
   topically applying, to an area of the subject's skin affected by actinic keratosis, an effective amount of a composition comprising calcipotriol and KX01, which has the following structure:

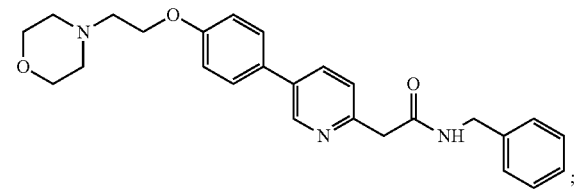 [SMILES: O=C(Cc1ccc(-c2ccc(OCCN3CCOCC3)cc2)cn1)NCc1ccccc1]

and
   wherein the calcipotriol and the KX01 are present in synergistic concentrations that are therapeutically effective.

2. The method of claim 1, wherein the composition is topically applied at a frequency of once per week to four times per day.

3. The method of claim 1, wherein the composition further comprises a retinoid.

4. The method of claim 3, wherein the retinoid has at least one activity selected from the group consisting of induction of keratinocytes proliferation, modulation of epidermal differentiation, stimulation of extracellular matrix production, and alteration of sebocyte differentiation.

5. A method of treating psoriasis in a subject in need thereof, the method comprising:
   topically applying, to an area of the subject's skin affected by psoriasis, an effective amount of a composition comprising calcipotriol and KX01, which has the following structure:

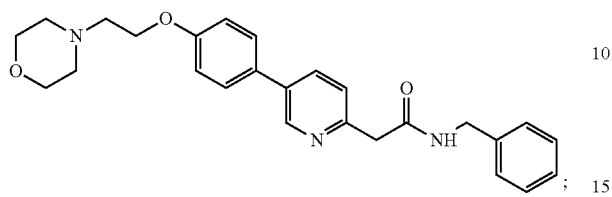

and
   wherein the calcipotriol and the KX01 are present in synergistic concentrations that are therapeutically effective.

6. The method of claim 5, wherein the composition is topically applied at a frequency of once per week to four times per day.

7. The method of claim 5, wherein the composition further comprises a retinoid.

8. The method of claim 7, wherein the retinoid has at least one activity selected from the group consisting of induction of keratinocytes proliferation, modulation of epidermal differentiation, stimulation of extracellular matrix production, and alteration of sebocyte differentiation.

* * * * *